United States Patent
Breibart

(10) Patent No.: US 10,667,941 B1
(45) Date of Patent: Jun. 2, 2020

(54) WEARABLE EXERCISE AND POSTURE-AWARENESS ASSIST DEVICE

(71) Applicant: Joan Breibart, New York, NY (US)

(72) Inventor: Joan Breibart, New York, NY (US)

(*) Notice: Subject to any disclaimer, the term of this patent is extended or adjusted under 35 U.S.C. 154(b) by 0 days.

(21) Appl. No.: 16/535,520

(22) Filed: Aug. 8, 2019

Related U.S. Application Data

(60) Provisional application No. 62/719,234, filed on Aug. 17, 2018.

(51) Int. Cl.
*A61F 5/00* (2006.01)
*A61F 5/02* (2006.01)
*A63B 23/02* (2006.01)

(52) U.S. Cl.
CPC .............. *A61F 5/026* (2013.01); *A63B 23/02* (2013.01); *A61H 2201/0192* (2013.01); *A61H 2201/1614* (2013.01); *A61H 2201/1652* (2013.01)

(58) Field of Classification Search
CPC ... A61F 5/026; A61F 5/00; A61F 5/06; A61H 1/0218; A61N 1/3987; A61N 1/0484; A61N 1/3904; A61N 1/046; A61N 1/3993; A61N 1/3925; A61N 1/3975; A61N 1/3968; A61N 1/39; A61N 1/025; A61N 1/39046; A61N 1/3918; A61N 1/0496; A61N 1/08; A61N 1/3625; A61N 1/36542; A61N 1/39044
USPC .................................................. 482/38; 602/4
See application file for complete search history.

(56) References Cited

U.S. PATENT DOCUMENTS

| | | | | |
|---|---|---|---|---|
| 1,618,273 A | * | 2/1927 | Davidson | A63B 21/0004 482/124 |
| 2,097,376 A | * | 10/1937 | Marshman | A63B 21/0004 482/124 |
| 2,723,664 A | * | 11/1955 | Davis | A61F 13/143 602/19 |
| 3,338,236 A | * | 8/1967 | McLeod, Jr. | A61F 5/05808 602/19 |
| 4,010,744 A | * | 3/1977 | Boyen | A61F 5/3715 602/36 |
| 4,901,713 A | * | 2/1990 | Troeger | A61F 5/3738 602/4 |
| 5,371,565 A | * | 12/1994 | Matsubara | G03B 9/18 396/484 |
| 5,647,827 A | * | 7/1997 | Gutkowski | A63B 21/0004 482/122 |
| 5,916,070 A | * | 6/1999 | Donohue | A63B 21/151 482/114 |
| 7,549,948 B2 | * | 6/2009 | Makofsky | A63B 23/0244 2/69 |
| 7,744,511 B2 | * | 6/2010 | Grigoriev | A61F 5/0102 482/121 |

(Continued)

Primary Examiner — Kim M Lewis
(74) Attorney, Agent, or Firm — R. Neil Sudol; Henry D. Coleman

(57) ABSTRACT

An exercise device includes a belt and a shoulder harness, the latter attachable to a user about the thorax. The belt is extensible about a user below user's chest or thorax. Two bungee cords are attachable one at its ends to the user's hands, and the other at its ends to the user's feet. An elongate strip has a pair of parallel adjacent channels, the hand bungee traversing the upper channel and the feet bungee traversing the lower channel. The two channels are connected a back portion of the shoulder harness. Two shoulder straps are each fixed at one end to the belt and are continuous with the back portion of the shoulder harness.

18 Claims, 4 Drawing Sheets

(56) References Cited

U.S. PATENT DOCUMENTS

| | | | | |
|---|---|---|---|---|
| 7,744,512 | B2 * | 6/2010 | Clarke | A63B 23/1209 |
| | | | | 482/124 |
| D635,203 | S * | 3/2011 | Breibart | A63B 21/151 |
| | | | | D21/662 |
| 8,784,285 | B1 * | 7/2014 | Lopez | A63B 21/0555 |
| | | | | 482/121 |
| 9,204,987 | B1 * | 12/2015 | Breibart | A61F 5/055 |
| 10,195,475 | B2 * | 2/2019 | Schreiber | A63B 21/0557 |
| 2006/0047236 | A1 * | 3/2006 | Hansen | A61B 90/00 |
| | | | | 602/4 |
| 2009/0062087 | A1 * | 3/2009 | Poppinga | A63B 21/0552 |
| | | | | 482/124 |

\* cited by examiner

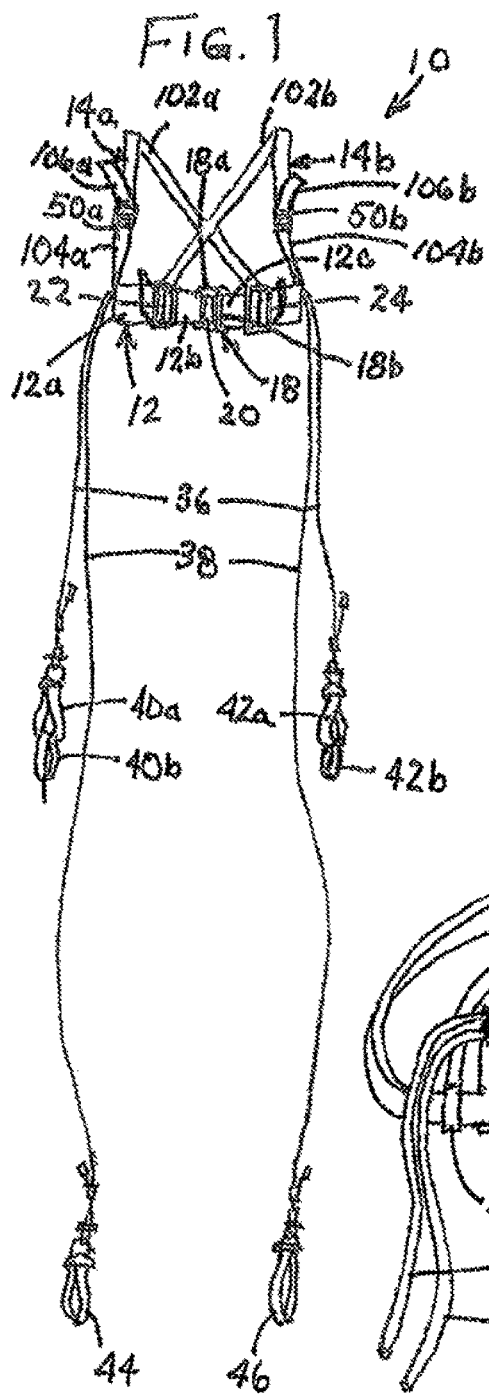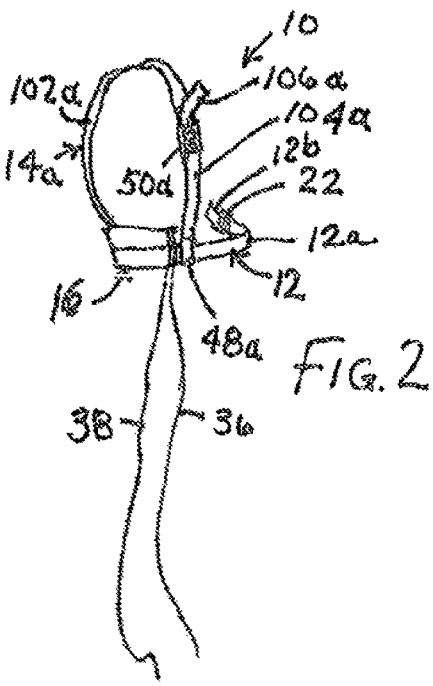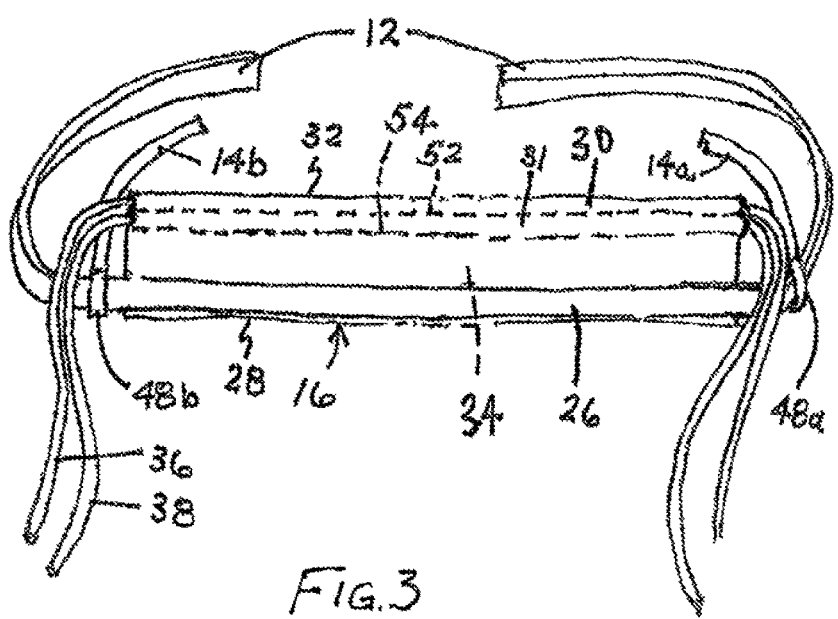

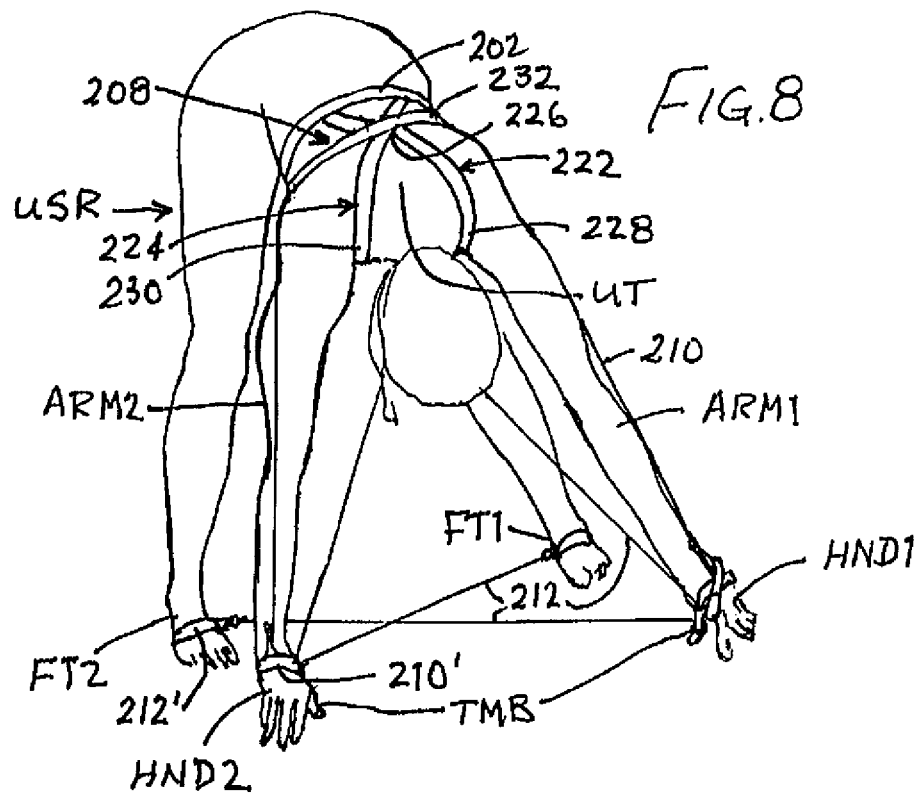
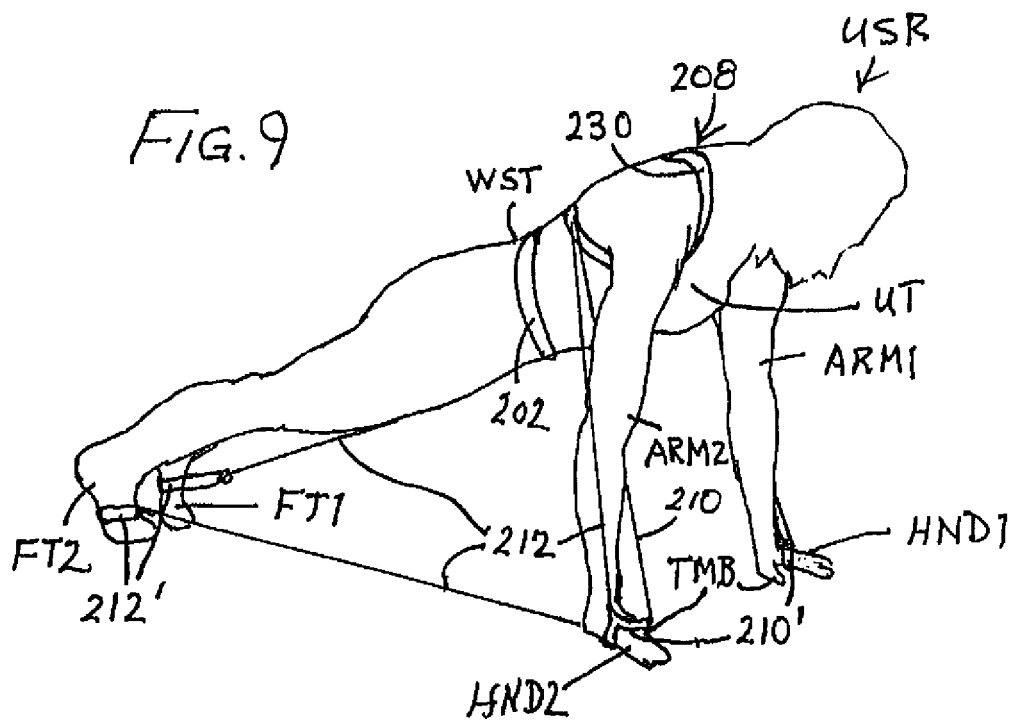

WEARABLE EXERCISE AND POSTURE-AWARENESS ASSIST DEVICE

BACKGROUND OF THE INVENTION

This invention relates to a wearable device for use in facilitating or assisting a user in improving the user's posture and enhancing posture awareness. The device is typically used in exercise or movement routines.

People today suffer from a number of nervous ailments owing to current occupations that involve much sitting and typing and looking at computer screens. Many of these ailments can be traced to poor posture. A number of so-called posture correctors are currently on the market that purport to address the problem. Such devices typically take the form of a chest and back harness that forces, or attempts to force, the user's upper spine into a configuration resulting in a reduction of adverse spinal nerve conditions. These devices do not work. They are more like straightjackets that imprison the user. Rather than gently soothing the user and making her comfortable in the workplace, the harnesses causes discomfort and even exacerbates the user's pain by inducing the user's musculature to seize up.

The problem of poor posture giving rise to chronic pain cannot be addressed by the technique of conventional posture improvement devices.

Dancers and athletes, owing to the extreme physical nature of their occupations and avocations, require control of posture, particularly torso orientation and configuration, in addition to controlling limb movement.

U.S. Pat. No. 9,204,987 discloses in pertinent part an exercise assist device including a harness attachable to a user about the thorax so that the harness extends about the thorax. The harness includes a chest strap that extends like a belt about the chest of the user just below the armpits. Two tensile members, preferably implemented as so-called bungee cords, extend through respective channels provided along a rear surface of a back side portion of the chest strap. One of the two tensile members is attachable at its opposite ends to the hands of the user, for instance, via respective loops, rings or bands. The other tensile member is attachable at its opposite ends to the feet or ankles of the user, again via respective loops, rings or bands. The harness further includes two shoulder straps extending in U-shaped configurations parallel to one another, each shoulder strap being connected at one end to the back portion of the chest strap and at an opposite end to a front portion of segment of the chest strap.

After the issuance of U.S. Pat. No. 9,204,987, it was discovered that the device of that patent could be used in executing an extensive range of exercise movements. The movements included many specifically designed to improve the user's performance in different kinds of dance and sports, particularly if the bungee cords were strengthened (to exhibit a larger spring constant) so as to provide a greater resistance to motion of a user's arms and legs. The promise of the device was substantial. However, in practice there arose an impediment to widespread adoption of the device. The device became uncomfortable when the user would undertake certain kinds of movements and, more importantly, the harness would shift so that execution of the exercises was impeded regardless of whether the front of the harness was above or beneath a female user's breasts. If front strap placement was above, the harness would slip downwards and hit the breast tissue. If front strap placement was below the breasts, the harness would slip downwards and resistance was lost.

As depicted in the patent, the front portion or segment of the chest strap was contemplated to extend over the breasts of a female user. However, some women users find this to be uncomfortable. The shoulder straps extend in parallel on opposite sides of the user's body in vertically oriented U-shaped configurations over the shoulders and tend to fall off. Moreover, tightening the shoulder straps causes the back of the harness to rise and pull the front of the chest strap up against the undersides of the breasts. This use of the device tends to round the user's back and shoulders, which is opposite the desirable postural effect of pulling the chest up and outwards and the shoulders back and down.

Furthermore, if adjustments are made to the lengths and positions of the shoulder straps so that the front portion or segment of the chest strap can lie below the breasts, the bungee cords are not at a height for optimal working, severely limiting the functionality of the device in contemplated dance- and sports-related performance-improvement exercises. These problems are compounded by the fact that breast sizes vary and that larger breasts require an increasingly lower placement of the chest strap when it is positioned below the breasts. This aggravates the problem as to the functionality of the two bungee settings. They are too low and pull the harness down so that it is uncomfortable.

OBJECTS OF THE INVENTION

It is an object of the present invention to provide a device for use in facilitating or assisting a user in improving the user's posture and enhancing posture awareness.

It is an object of the present invention to provide such a device that is typically used in exercise or movement routines.

Another particular object of the present invention is to provide an improved chest harness and bungee-cord device of the above-described type that solves the above-described problems of the prior art.

A more particular object of the present invention is to provide such an improved wearable device for alignment and exercising in every plane of movement, particularly in dance and sports, thus improving over the prior art.

Another particular object of the present invention is to provide such an improved device that not only solves the above-described problems of the prior-art bungee-supporting chest harness in the performance of a wide range of exercises that improve performance in dance and sports activity but also improves strength and flexibility needed for everyday life.

These and other objects of the present invention will be apparent to one skilled in the art from the drawings and descriptions herein. Although every feature of the invention is attained in at least one embodiment of the invention, there is not necessarily any one embodiment that achieves all of the objects of the invention.

SUMMARY OF THE INVENTION

The present invention is directed to a bungee-supporting chest or thorax harness that may be used in a wide variety of exercises in standing, seated, side-lying, supine prone, and lateral bending postures, and in rotational movements. There are an enormous number and range of human movements that may be improved, if not optimized or perfected, with resistance and awareness assistance provided by a wearable device pursuant to the invention, particularly for female users.

A wearable device for assisting a user in performing a wide variety of exercises and in improving posture awareness and concomitantly performance in dance and various sports comprises, in accordance with a particular embodiment of the present invention, a belt, a pair of fastener components, a shoulder harness, a pair of tensile members, and an elongate strip.

The fastener components are attached to opposite ends of the belt and releasably couplable to one another so as to close the belt in an endless configuration. The shoulder harness is attached to the belt and attachable to a user at the height of the user's thorax. The shoulder harness consists essentially of a single continuous strap or band connected at opposite ends to a back portion of the belt. The single continuous strap or band includes a first end segment and a second end segment each extending from the belt, as well as overlapping and in contact with one another at a crossing. The first end segment and the second end segment each define a respective shoulder loop on a side of the crossing opposite the belt. The single continuous strap or band has a middle segment continuous on opposite ends with the first end segment and the second end segment, respectively. The middle segment extends parallel to and spaced from the back portion of the belt in a use configuration of the wearable device.

The tensile members are elongate and at least partially elastic. One tensile member is attachable at ends at least indirectly to the user's hands, while the other tensile member is attachable at ends at least indirectly to the user's feet.

The elongate strip has an elongate upper channel and an elongate lower channel extending parallel to one another. The one tensile member slidably traverses the elongate upper channel, while the other tensile member slidably traverses the elongate lower channel. The elongate strip is attached to the middle segment of the single continuous strip or band.

Preferably, the first end segment and the second end segment are fixed (e.g., stitched or sewn) to one another at the crossing.

In a use configuration of the wearable device, the middle segment overlaps and engages the first end segment and the second end segment at the crossing. The middle segment is not attached to the first end segment and the second end segment at the crossing and so is freely movable relative to the crossing.

Pursuant to further features of the present invention, the elongate strip is substantially coextensive with the middle segment of the single continuous strip or band, the elongate strip is stitched or sewn to the middle segment, the first end segment and the second end segment are each stitched or sewn to the back portion of the belt, and the elongate strip is lengthwise co-extensive with each of the elongate upper channel and the elongate lower channel.

Pursuant to another feature of the invention, the middle segment and the elongate strip attached thereto are spaced from the back portion of the belt by at least two inches in the use configuration of the wearable device. The middle segment and the elongate strip have a common length that is approximately equal to the width of the user's back.

It is contemplated and preferred that the single continuous strip or band, including the first end segment, the second end segment and the middle segment, and the back portion of the belt are devoid of rigid elements. Thus, the shoulder harness and the back of the belt have no fasteners, buckles or reinforcements that would bite into the flesh of the user and introduce discomfort so as to discourage use of the wearable device.

The upper channel and the lower channel preferably have straight or linear configurations. This enables, facilitates, or promotes slidability of the tensile members along the elongate strip and thus reduces, if not eliminates, potential interference with various exercise routines.

In accordance with an additional feature of the present invention, the single continuous strip or band has a uniform width along an entire length of the single continuous strip or band. Not only does this feature facilitate manufacture but evens out or distributes stress during use of the device, enhancing comfort.

An exercise and/or posture awareness enhancement method in accordance with the present invention comprises (i) providing a shoulder harness, the shoulder harness having a plurality of bungees attached. The method further comprises (ii) attaching the shoulder harness about a user's torso or thorax, (iii) attaching ends of the bungees to the user's hands and feet. Typically one bungee has loops or bands at opposite ends through which the feet are inserted with the loops or bands encircling the feet at the instep. The other bungee has loops or bands at opposite ends through which the hands are inserted.

More specifically, a method in accordance with the present invention for improving awareness of posture and body alignments utilizes a device including a belt, a fastener attached to the belt, and a shoulder harness attached to the belt and including a pair of shoulder loops. The device further includes a first elongate and at least partially elastic tensile member, a second elongate and at least partially elastic tensile member, and an elongate strip having an elongate upper channel and an elongate lower channel extending parallel to one another. The first tensile member slidably traverses the elongate upper channel, while the second tensile member slidably traverses the elongate lower channel. The elongate strip is attached at least at opposite ends to the shoulder loops. The method further comprises inserting two arms of a user through respective ones of the shoulder loops so that the elongate strip extends straight across the user's back at the level of the user's chest or thorax. The belt is wrapped about the torso of the user below the user's chest or thorax (and as low as the user's waist) at a distance of at least one and preferably a few or several inches from the elongate strip. The fastener is operated to releasably close the belt in an endless configuration about the user. Opposite ends of the first tensile member are attached at least indirectly to the user's hands, while opposite ends of the second tensile member are attached at least indirectly to the user's feet. The user moves his or her limbs and torso while maintaining tension on the tensile members.

Preferably the shoulder harness includes a single continuous strap or band connected at opposite ends to a back portion of the belt. The single continuous strap or band has two end segments each extending from the belt, overlapping and in contact with one another at a crossing. The end segments each define a respective one of the shoulder loops on a side (the upper side) of the crossing opposite the belt. The single continuous strap or band has a middle segment continuous on opposite ends with respective ones of the end segments, while the elongate strip is attached to and extends along and in contact with the middle segment.

Pursuant to a more general embodiment of the present invention, a wearable device for assisting a user in maintaining awareness of skeleton-muscular alignment comprises a belt, a fastener attached to the belt so as to close the belt in an endless configuration, an elongate strip, a pair of shoulder straps or loops, and a pair of tensile members. The elongate strip evinces an elongate upper channel and an elongate lower channel extending adjacent and parallel to one another, the elongate strip being disposable on a backside of a user so as to extend parallel to and above a back or rear-side portion of the belt disposable on the backside of a user. The shoulder straps or loops are attached each at one end to the belt. The shoulder straps are each connected to the other and to the elongate strip at an end opposite the one end, i.e., at an end opposite the end attached to the belt. The tensile members are elongate and at least partially elastic members one attachable at ends at least indirectly to the user's hands, the other at least indirectly to the user's feet, the tensile member for the hands slidably traversing the elongate upper channel in the elongate strip and the tensile member for the feet slidably traversing the elongate lower channel.

Pursuant to several features of the invention, the shoulder straps or loops are fixed to one another at a crossing spaced from the belt, the shoulder straps or loops connect to a strap segment that overlaps and engages the shoulder straps or loops at the crossing, such that the strap segment is freely movable relative to the shoulder straps or loops at the crossing.

The shoulder straps or loops are preferably end portions of a single continuous strap or band and engage one another in overlap at a crossing. The strap segment constitutes a middle segment of the single continuous strap or band and is continuous on opposite ends with the end portions (the shoulder straps or loops). The elongate strip is attached to and extends along and in contact with the middle segment.

It is contemplated that the tensile members are coupled to the hands and feet of the user via non-elastic bands at the free ends of the tensile members. Other alternative forms of attachment might be suitable in limited applications, for example, gloves and socks or booties, rings, straps, looped-back end portions of the tensile members, etc.

A wearable device in accordance with the present invention can be used in innumerable ways in countless different exercises that improve one's posture awareness, in part through facilitating one's awareness of relative positioning of the limbs and the tensions or muscular contractions that are required in each movement. This is a huge advantage for individuals who are not natural athletes but wish to take up one sport or another. Proper posture is a sine qua non for excelling in any sport. Thus the present invention is useful for preparing and adapting people to the sports they select.

A wearable exercise device pursuant to the present invention, in contrast to other wearable devices, is not attachable solely, necessarily or even mainly at the user's waist inasmuch as the present device includes a shoulder harness. In contrast to waist-located devices, during use of the present device one feels that the upper parts of the body rise and that the legs float. In contrast to dumbbells and weights attached to ankles and wrists, which can cause injury owing to the extreme distribution of extra weight, the present device distributes resistance along the lengths of the limbs. The device is holistic in that the entire body responds, including the mind. The user is aware of the body's response throughout the body, not in isolated muscles.

In contrast to the device of U.S. Pat. No. 9,204,987, the present device gives rise to a redistribution of resistance. The bungees are located high, under the armpits, while the belt or band is worn much lower, beneath the breasts of female users, at or above the user's waist.

A wearable exercise device pursuant to the present invention serves to lift the body rather than compressing it down. In contrast to chest harnesses sold for improving posture, the exercise device of the present invention does not apply force to the user to change the user's posture. The present invention aims at improving posture by gently improving the user's awareness of her posture and muscular tone and activation. Improved awareness arises in part from smooth and distributed resistance in a large range of movement exercises. For instance, a leg lift can be lent assistance by pulling up on the associated bungee segment attached to the respective foot. A user rests a lifted leg by extending the associated bungee segments sideways into space so that it cannot move. Then more muscle power is required to lift the leg.

BRIEF DESCRIPTION OF THE DRAWING

FIG. 1 is a front elevational view of a posture awareness and improvement assist device for use in exercising, in accordance with the present invention.

FIG. 2 is a partial side elevational view of the device of FIG. 1.

FIG. 3 is a partial rear elevational view of the device of FIGS. 1 and 2, on a larger scale.

FIG. 8 is a schematic perspective view of a user wearing the device of FIGS. 4 and 5 in executing a third exemplary exercise.

FIG. 9 is a schematic perspective view of a user wearing the device of FIGS. 4 and 5 in conducting a fourth exemplary exercise.

DETAILED DESCRIPTION

Figure 4:
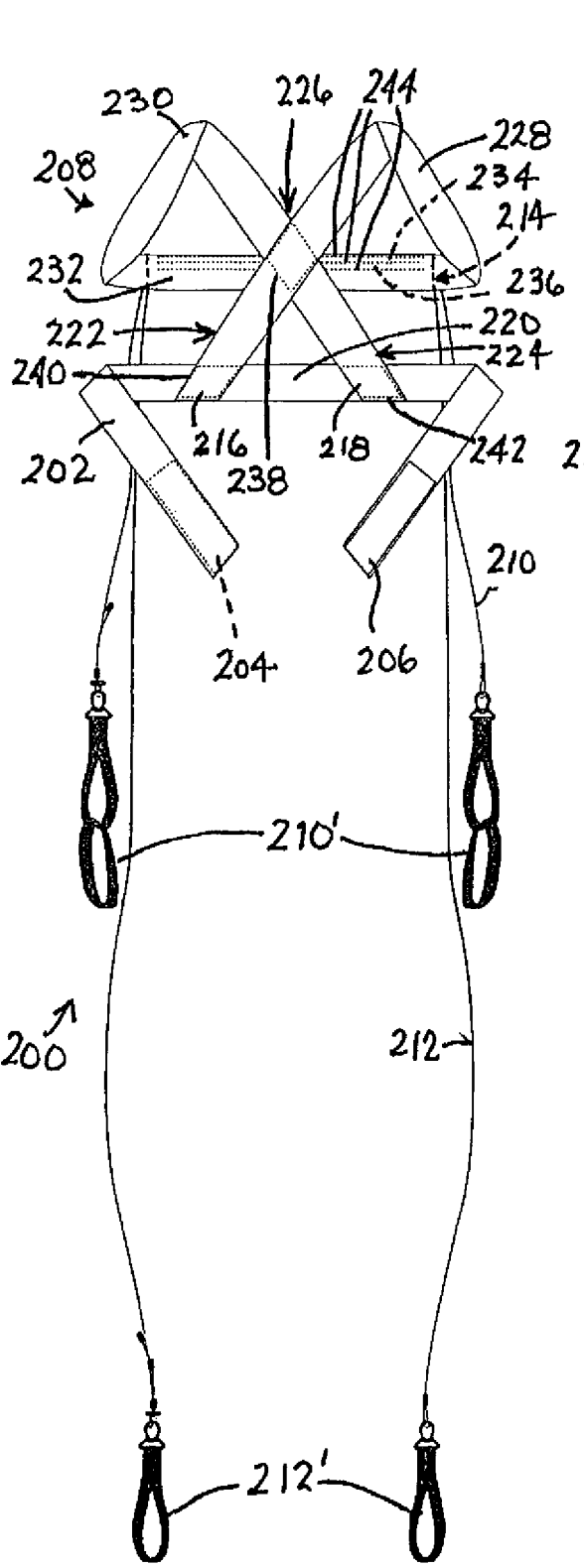
FIG. 4 is a front elevational view of another device for use in exercises to enhance posture awareness, in accordance with the present invention.

As depicted in FIGS. 1-3, a chest, torso or thorax harness 10 particularly designed for assisting a female user in maintaining awareness of posture during a wide range of exercises includes a circumferentially extending main strap or belt member 12 that encircles the user in a generally horizontal plane about a lower portion of the user's chest or thorax. Chest harness 10 further includes a pair of shoulder straps 14a and 14b each connected at one end to an elongate tripartite back strip 16 that is part of harness 10. During use of harness 10 by a female user, belt member 12 is disposed about the user's thorax and below the user's breasts. A fastener 18 in the form of a snap-lock buckle is attached to belt member 12 for effectuating a closure of the same in an endless loop. Fastener or buckle 18 may have a release 20 that opens or unlocks the buckle upon application of finger pressure.

Two length-adjustment elements 22 and 24 are provided on the front side of belt member 12 for adapting the circumference of the closed belt member 12 to the chest size of the user. Length-adjustment elements 22 and 24 are provided at mirror symmetric positions relative to buckle 18 for enabling symmetrical adjustments to the fit of main strap or belt member 12 to the chest or thorax of the user.

Chest strap or belt member 12 includes three belt segments 12a-12c: a first segment 12a extending from one length adjustment element 22 around the back of the user to the other length adjustment element 24, a second segment 12b connected to one length adjustment element 22, and a third segment 12c connected to the other length adjustment element 24. Fastener or buckle 18 has a first part 18a attached to an end of the second belt segment 12b and a second part 18b attached to an end of the third belt segment 12c.

Tripartite back strip 16 is made in part of flexible fabric material and includes a lowermost portion formed by a back or rear-side segment 26 of belt member 12 that extends longitudinally along a lower edge 28 of the back strip. Back strip 16 further includes an elongate upper strip portion comprising two elongate channels 30 and 31 (FIG. 3) extending longitudinally along an upper edge 32 of back strip 16. Thus, channels 30 and 31 extend parallel to and above belt back or rear-side segment 26 during use of the device 10. Belt segment 26, on the one hand, and channels 30 and 31, on the other hand, are separated or spaced from one another, across the width of tripartite back strip 16, by an elongate section 34 of flexible material which forms a middle part of the back strip. In a preferred embodiment, each of the three sections of back strip 16 are about one-inch wide. Flexible middle or coupling section 34 may be more or less wide, for instance, to accommodate users of different sizes. Tripartite back strip 16, including each of its three sections 30 and 31, 26 and 34 is typically 13 inches long, but that dimension may be varied somewhat, again to accommodate people of different dimensions.

Thorax or chest harness 10 includes two elongate and at least partially elastic tensile members 36 and 38, exemplarily in the form of bungee cords, that traverse channels 30 and 31, respectively. Channels 30 and 31 are two adjacent parallel passageways one above the other with the upper one 30 slidably traversed by tensile member or cord 36 and the lower one 31 slidably traversed by tensile member or cord 38. Channels 30 and 31 may be formed by a rectangular blank of flexible material along the upper longitudinal edge of back strip 16 that is folded back on itself and sewn along a pair of parallel stitch lines 52, 54.

Tensile member or bungee cord 36 is provided at its opposite ends with two interlinked loops 40a, 40b and 42a, 42b of inelastic material that are attachable at least indirectly to the user's hands. The user may insert her hands alternately into loops 40a and 42a or loops 40b and 42b (or both) and curl her fingers around the loops in a firm grip. Tensile member or bungee cord 38 is provided at its opposite ends with loops 44 and 46 of inelastic material that are attachable at least indirectly to the user's feet, for instance, via passing the feet through the loops so that the loops encircle the feet at the instep.

Shoulder straps 14a and 14b, each fixed at one end to back strip 16, are provided at opposite ends with respective loops or eyelets 48a and 48b slidably traversed by belt member 12. Shoulder straps 14a and 14b cross one another on the back side of chest or thorax harness 10, in a location laterally of the width dimension of back strip 16 and above the strip. Each loop or eyelet 48a and 48b is looped around belt member 12 at a location proximate a respective end of back strip 16 and may be formed by folding back an end of the respective shoulder strap 14a, 14b and sewing the strap end to itself.

As back strip 16 has a length dimension approximately equal to the width of the user's back from side to side, the shoulder strap loops 48a and 48b are located beneath the user's armpits during use of the chest harness 10. Shoulder straps 14a, 14b are provided with respective length adjusters 50a, 50b enabling the user to adjust the effective lengths of the shoulder straps as desired.

Each shoulder strap 14a and 14b comprises a respective pair of strap segments 102a, 104a and 102b, 104b that are connected to one another via the respective length adjuster 50a, 50b. Strap segments 102a and 102b of shoulder straps 14a and 14b are connected to back strip 16 and each 102a and 102b has a length so as to be extendable over the shoulder of the user. The other strap segments 104a and 104b are formed with belt-attachment loops 48a and 48b of the respective shoulder straps 14a and 14b. A combined length of two strap segments 102a and 104a (the length of shoulder strap 14a) or two strap segments 102b and 104b (the length of shoulder strap 14a) is shortened by pulling a terminal portion 106a or 106b of the respective strap segment 102a, 104a in an upward direction away from the respective length adjuster 50a or 50b.

Chest harness 10 is particularly beneficial for female users owing to the separation of channels 30 and 31 and concomitantly the vertical spacing between chest strap or belt member 16, on the one hand, and elastic tensile members 36 and 38, on the other hand. Back strip 16 may have different sizes, that is, different lengths and different widths, to accommodate women of different chest and breast sizes, so that belt member 12 is located comfortably below the user's breasts and so that channel 30 is high enough to facilitate alignment of elastic tensile members or bungee cords 36 and 38 with the user's arms when horizontally extended in opposed directions on respective sides of the user.

Flexible portion 34 of tripartite back strip 16, between channels 30 and 31 at the top and back or rear-side segment 26 of belt member 12 at the bottom, is a coupling that facilitates functional separation of bungees 36 and 38 from chest strap or belt member 12 but also contributes to user comfort as flexible fabric-like material is generally more comfortable than rigid or stiff material. Flexible portion 34 is preferably made of fabric material, but may take alternative forms such as netting, plural fingers or strips of flexible material spaced from one another along the lengths of channels 30 and 31 at the top and back or rear-side segment 26 of belt member 12.

The vertical location of channels 30 and 31 and accordingly tensile members or bungee cords 36 and 38 is above the vertical location of belt segment 26 and concomitantly the entire chest strap or belt member 12.

During use of the chest harness or posture-awareness and -improvement device 10, bungee cord 36 is attached at opposite ends via bands or loops 40a, 40b and 42a, 42b to the hands (or wrists) of the user, while bungee cord 38 is attached to the user's feet via bands or loops 44 and 46. Tripartite back strip 16 extends horizontally across the user's back, and bungee cords 36 and 38 are slidably connected to the back strip 16 via channels 30 and 31. Channels or passageways 30 and 31 each have outlet openings (not designated) at opposite sides of back strip 16.

In use of a device in accordance with the present invention, strap or belt member 12 is locatable at the breastbone in front, beneath the breasts of a female user, while bungee cords or bungee cords 36 and 38 are disposable over the shoulder blades in back of the user.

While the user holds her limbs in prescribed positions, bungee cords 36 and 38 apply forces to the user's arms, legs and torso that provide kinesthetic and resistive feedback to the user, increasing the user's awareness of body posture and thereby assisting the user in adopting and holding a desired configuration or orientation set. The user may enhance the awareness and feeling by looking at herself in a mirror while holding one or more different positions for short times.

Chest-harness bungee cord or arm bungee cord 36 crosses the user's back at the scapular region; this creates tension and when the two ends of this bungee cord are pulled forward and lifted overhead, with a right angle at the elbows, they cause the scapular region to indent and release (it is usually locked given most people's posture).

Figure 5:
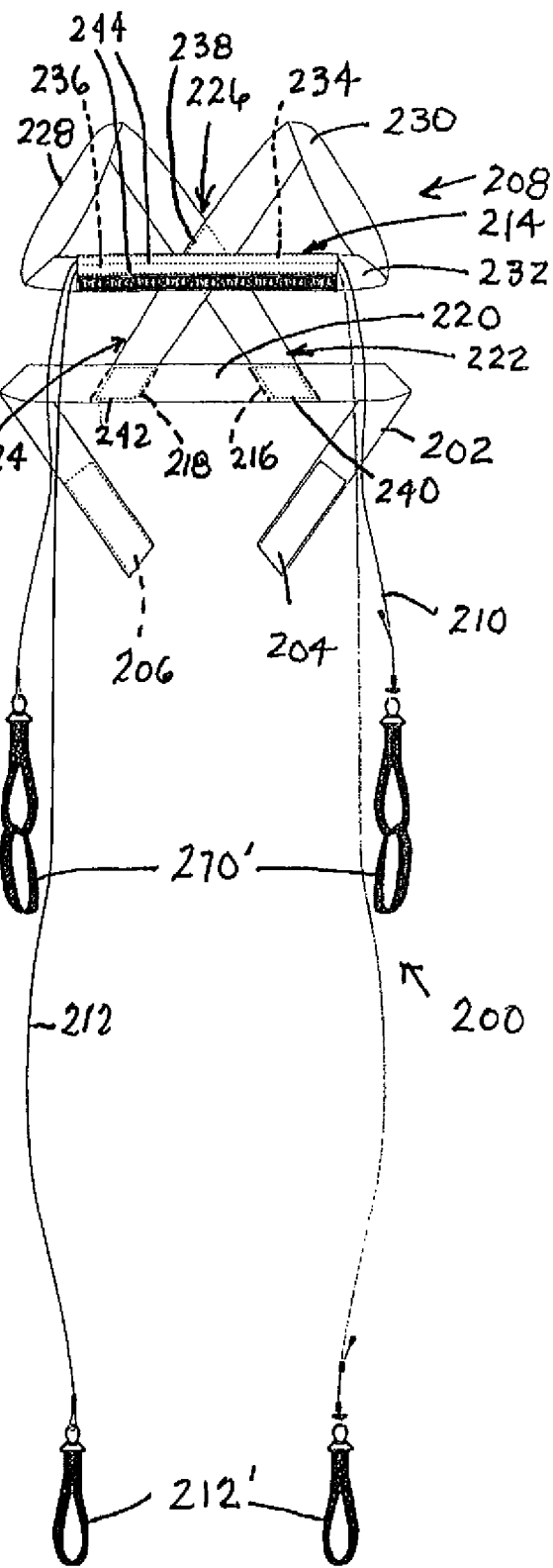
FIG. 5 is a rear elevational view of the device of FIG. 4.
Figure 6:
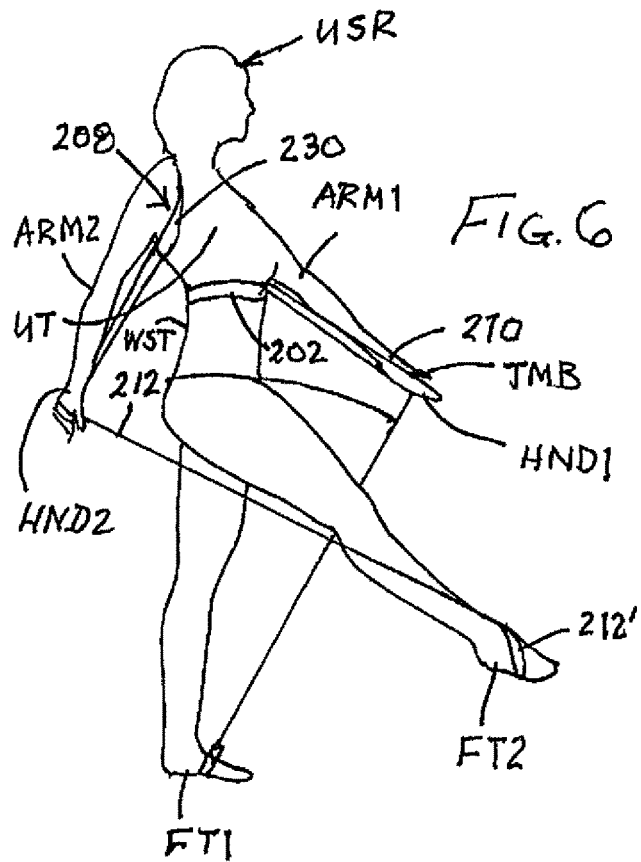
FIG. 6 is a schematic perspective view of a user wearing the device of FIGS. 4 and 5 in performing a first exemplary exercise.
Figure 7:
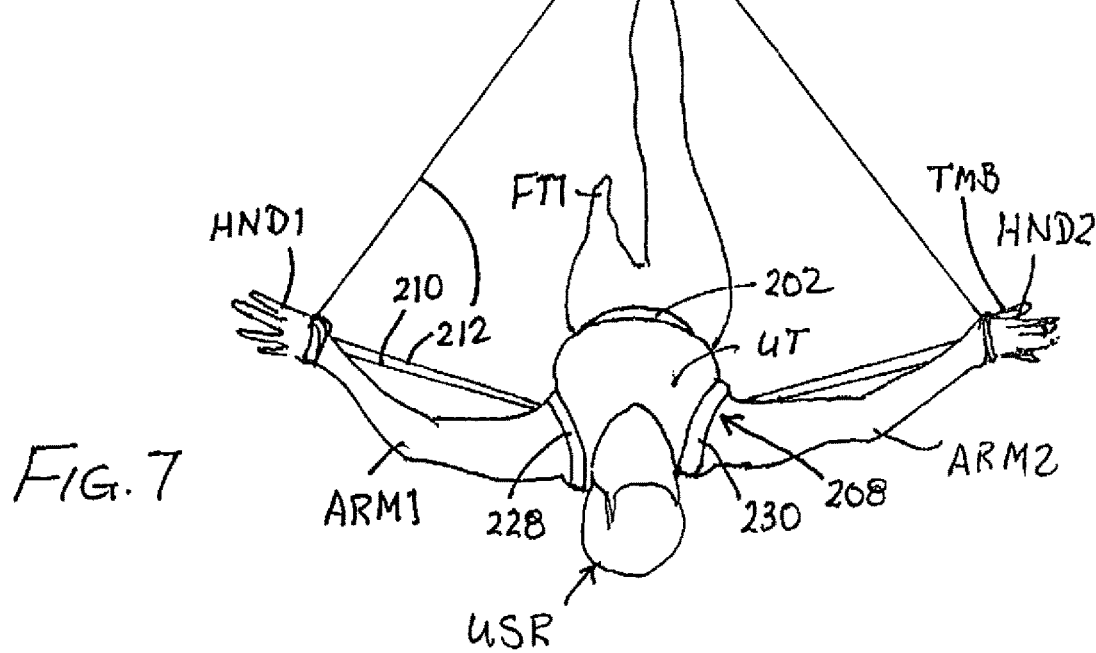
FIG. 7 is a schematic perspective view of a user wearing the device of FIGS. 4 and 5 in carrying out a second exemplary exercise.

As illustrated in FIGS. 4 and 5, a wearable device 200 for assisting a user USR (FIGS. 6-9) in performing a wide variety of exercises and in improving posture awareness and concomitantly performance in dance and various sports includes a belt 202, a pair of fastener components 204 and 206, a shoulder harness 208, a pair of tensile members (bungees) 210 and 212, and an elongate bungee guide strip 214.

Fastener components 204 and 206 specifically take the form of hook and loop fasteners commonly known as VELCRO™ and are respectively fixed to opposite ends of belt 202 and releasably couplable to one another so as to close the belt in an endless torso-encircling configuration. Shoulder harness 208 is connected to belt 202 and attachable to user USR at the chest or thorax region.

Shoulder harness 208 consists essentially of a single continuous strap or band (not separately labeled) stitched or sewn at opposite ends 216 and 218 to a back portion 220 of belt 202. The single continuous strap or band includes a first end segment 222 and a second end segment 224 each extending from belt 202. End segments 222 and 224 overlap, in contact with one another, at a crossing or cross-over point 226.

End segments 222 and 224 each define a respective shoulder loop 228 and 230 on a side of crossing 226 opposite belt 202. The single continuous strap or band of shoulder harness 208 has a middle segment 232 continuous on opposite ends with end segment 222 and end segment 224, respectively. Middle segment 232 extends parallel to, and spaced preferably 2-3 inches from, back portion 220 of belt 202 in a spread-out configuration of the wearable device, as depicted in FIGS. 4 and 5, and during use of the device as shown in FIGS. 6-9.

Tensile members 210 and 212 take the form of bungee cords, which are elongate and at least partially elastic elements. One tensile member 210 is temporarily attachable at ends at least indirectly to hands HND1 and HND2 of user USR, while tensile member 212 is releasably attachable at ends at least indirectly to the user's feet FT1, FT2, as shown in FIGS. 6-9.

Elongate strip 214 has an elongate upper channel 234 and an elongate lower channel 236 extending parallel to one another. Hand tensile member 210 slidably traverses upper channel 234, while foot tensile member slidably traverses lower channel 236. Elongate strip 214 is joined to middle segment 232 of the single continuous strap or band of shoulder harness 208.

End segments, or shoulder loop portions, 222 and 224 are fixed to one another, preferably by stitching or sewing 238, at crossing or cross-over point 226. Stitching 240 and 242 also connects ends of end segments or shoulder loop portions 222 and 224 to back portion 220 of belt 202.

In a use configuration of the wearable device 200, middle segment 232 overlaps and engages end segments or shoulder loop portions 222 and 224 at crossing or cross-over point 226. Middle segment 232 is unattached to end segments 222 and 224 at crossing 226 and accordingly may freely movable relative to the crossing.

Elongate bungee-guide strip 214 is substantially coextensive with middle segment 232 of shoulder harness 208. Strip 214 is stitched or sewn to middle segment 232 along parallel seam lines 244. Upper channel 234 and lower channel 236 constitute straight or linear tubes both lengthwise coextensive with strip 214 and formed by the stitching of elongate strip 214 along seam lines 244, with appropriate lengthwise deformation or corrugation of the material.

Middle segment 232 and elongate strip 214 attached thereto are spaced from back portion 220 of belt 202 by two to four inches, preferably about 2 and ¾ inches. Middle segment 232 and strip 214 have a common length approximately equal to the width of a typical user's back, or approximately 13 inches.

Shoulder harness 208 and back portion 202 of belt 202 are preferably devoid of rigid elements, specifically fasteners such as buckles, rings, and reinforcements that posture control devices typically include. While fasteners 204 and 206 may take a rigid form, such a buckle or clasp, or a hook and eyelet, the provision of such at other locations on shoulder harness 208 and belt 22 could distract a user and reduce the user's attention to posture, limb and head alignment, state of muscle contraction, etc., and thereby detract from device effectiveness in enabling a user to ultimately improve her posture.

Upper channel 234 and lower channel 236 preferably have straight or linear configurations. This enables, facilitates, or promotes slidability of bungee cords 210, 212 along the length of elongate strip 214 and thus reduces, if not eliminates, potential interference with various exercise routines.

The single continuous strip or band of shoulder harness 208 preferably has a uniform width along its entire length from end 216 to end 218.

An exercise and/or posture awareness enhancement method in accordance with the present invention comprises (i) providing shoulder harness 208, the shoulder harness having bungees 210 and 212 attached thereto, via slidable insertion through channels 234 and 236. User USR (FIGS. 6-9) attaches the shoulder harness 208 about the user's upper torso or thorax UT, and attaches ends of bungees 210, 212 to the user's hands HND1, HND2 and feet FT1, FT2. To that end, bungees 210, 212 are provided with loops or bands 210' and 212' at opposite ends through which the hands HND1, HND2 and feet FT1, FT2.

In using device 200, user USR inserts arms ARM1, ARM2 through shoulder loops 228, 230 so that elongate strip 214 extends transversely across the user's back at the thoracic spine. Belt 202 is wrapped about the torso of the user below the user's chest or thorax (and as low as the user's waist WST) at a distance of at least 2 and preferably about 2.75 to 3 inches from strip 214. Fasteners 204 and 206 are pressed together to releasably close the belt 202 in an endless configuration about the user USR. Opposite ends of tensile member or bungee 210 are attached at least indirectly to the user's hands HND1, HND2, while opposite ends of tensile member or bungee 212 are attached at least indirectly to the user's feet FT1, FT2. User USR moves her limbs and torso while maintaining tension on the tensile members or bungees 210, 212, in part by looping tensile member or bungee 212 around the user's thumbs TMB.

Belt 202 may have a different width than the single strap or band of shoulder harness 208 and may be made of a different fabric. Typically, the single strap or band of shoulder harness 208 has a width of 1.5 to 1.75 inches and a length of 62 inches and is made in part of elastic material so that lengthwise the various segments of the shoulder harness 208 may stretch lengthwise up to 50% of their relaxed or unstressed state.

Strip 214 is typically 1.5 inches wide and 13 inches long. Typically, channels 234 and 236 are defined and formed by three parallel seams 244.

The fabric stretches in the lengthwise direction only. With the afore-described dimensions, device 200 is adapted only for females of a certain size, for instance, with a maximum bra size of 36C. With these specification, device 200 is designed for dancers and thin females, so that they can move with self-aware gracefulness and without interference. Device 200 can be worn all day, with the user USR adjusting her posture with bungees 210 and 212.

Bungee cords 36, 38, 210, 212 may be replaced by any kind of tensile member that provides sufficient tension and therefore compressive support to a user's arms and legs. Bungee cords 36, 38, 210, 212 may be replaced by elastic polymeric tubes or hoses that are commonly used in the exercise field. However, bungee cords are preferable.

Although the invention has been described in terms of particular embodiments and applications, one of ordinary skill in the art, in light of this teaching, can generate additional embodiments and modifications without departing from the spirit of or exceeding the scope of the claimed invention. The arm and leg bungee cords 36, 38, 210, 212 may be provided, for example, at their free ends, with length-adjustment members for accommodating limbs of different lengths. Accordingly, it is to be understood that the drawings and descriptions herein are proffered by way of example to facilitate comprehension of the invention and should not be construed to limit the scope thereof.

What is claimed is:

1. A wearable device for assisting a user in improving posture and body alignments, comprising:
    a belt;
    a pair of fastener components attached to opposite ends of said belt, said fastener components being releasably couplable to one another so as to close said belt in an endless configuration;
    a shoulder harness attached to said belt, said shoulder harness being attachable to a user at the height of the thorax, said shoulder harness including a single continuous strap or band connected at opposite ends to a back portion of said belt, said single continuous strap or band having a first end segment and a second end segment each extending from said belt, said first end segment and said second end segment overlapping and in contact with one another at a crossing, said first end segment and said second end segment each defining a respective shoulder loop on a side of said crossing opposite said belt, said single continuous strap or band having a middle segment continuous on opposite ends with said first end segment and said second end segment respectively, said middle segment extending parallel to and spaced from said back portion of said belt in a use configuration of the wearable device;
    a first elongate and at least partially elastic tensile member attachable at ends at least indirectly to the user's hands;
    a second elongate and at least partially elastic tensile member attachable at ends at least indirectly to the user's feet; and
    an elongate strip having an elongate upper channel and an elongate lower channel extending parallel to one another, the first elongate and at least partially elastic tensile member slidably traversing the elongate upper channel, the second elongate and at least partially elastic tensile member slidably traversing the elongate lower channel, said elongate strip being attached to said middle segment of said single continuous strap or band.

2. The wearable device defined in claim 1 wherein said first end segment and said second end segment are fixed to one another at said crossing.

3. The wearable device defined in claim 2 wherein said first end segment and said second end segment are stitched to one another at said crossing.

4. The wearable device defined in claim 2 wherein in a use configuration of the wearable device said middle segment overlaps and engages said first end segment and said second end segment at said crossing, said middle segment being freely movable relative to said crossing.

5. The wearable device defined in claim 1 wherein said elongate strip is substantially coextensive with said middle segment of said single continuous strap or band.

6. The wearable device defined in claim 1 wherein said elongate strip is stitched or sewn to said middle segment.

7. The wearable device defined in claim 1 wherein said first end segment and said second end segment are each stitched or sewn to said back portion of said belt.

8. The wearable device defined in claim 1 wherein said elongate strip is lengthwise co-extensive with each of the elongate upper channel and the elongate lower channel.

9. The wearable device defined in claim 1 wherein said middle segment and said elongate strip attached thereto are spaced from said back portion of said belt by at least two inches in the use configuration of the wearable device.

10. The wearable device defined in claim 1 wherein said elongate strip and said middle segment of said single continuous strap or band have a common length that is approximately equal to the width of the user's back.

11. The wearable device defined in claim 1 wherein said single continuous strap or band, including said first end segment, said second end segment and said middle segment, and said back portion of said belt are devoid of rigid elements.

12. The wearable device defined in claim 1 wherein said upper channel and said lower channel have straight or linear configurations.

13. The wearable device defined in claim 1 wherein said single continuous strap or band has a uniform width along an entire length of said single continuous strap or band.

14. A method for improving awareness of posture and body alignments, comprising providing a device including a belt, a pair of fastener components attached to said belt, and a shoulder harness attached to said belt and including a pair of shoulder loops, said device further including:
    a first elongate and at least partially elastic tensile member;
    a second elongate and at least partially elastic tensile member; and
    an elongate strip having an elongate upper channel and an elongate lower channel extending parallel to one another, the first elongate and at least partially elastic tensile member slidably traversing the elongate upper channel, the second elongate and at least partially elastic tensile member slidably traversing the elongate lower channel, said elongate strip being attached at least at opposite ends to said shoulder loops,
    the method further comprising:
    inserting two arms of a user through respective ones of said shoulder loops so that said elongate strip extends straight across the user's back at the level of the user's chest or thorax;
    wrapping said belt about the torso of the user below the user's chest or thorax and spaced from said elongate strip;

releasably coupling said fastener components to one another so as to close said belt in an endless configuration about the user;

attaching opposite ends of said first elongate and at least partially elastic tensile member at least indirectly to the user's hands;

attaching opposite ends of said second elongate and at least partially elastic tensile member at least indirectly to the user's feet; and moving the user's limbs and torso while maintaining tension on said first elongate and at least partially elastic tensile member and said second elongate and at least partially elastic tensile member, said shoulder harness including a single continuous strap or band connected at opposite ends to a back portion of said belt, said single continuous strap or band having a first end segment and a second end segment each extending from said belt, said first end segment and said second end segment overlapping and in contact with one another at a crossing, said first end segment and said second end segment each defining a respective one of said shoulder loops on a side of said crossing opposite said belt, said single continuous strap or band having a middle segment continuous on opposite ends with said first end segment and said second end segment respectively, said elongate strip attached to and extending along and in contact with said middle segment.

15. A wearable device for assisting a user in maintaining awareness of skeleton-muscular alignment, comprising:
a belt;
a fastener attached to said belt so as to close said belt in an endless configuration;
an elongate strip having an elongate upper channel and an elongate lower channel extending adjacent and parallel to one another, said elongate strip being disposable on a backside of the user so as to extend parallel to and above a back or rear-side portion of said belt disposable on the backside of the user;
a pair of shoulder straps or loops attached each at one end to said belt, said shoulder straps each being connected to the other and to said elongate strip at an end opposite said one end;
a first elongate and at least partially elastic tensile member attachable at ends at least indirectly to the user's hands, the first elongate and at least partially elastic tensile member slidably traversing the elongate upper channel; and
a second elongate and at least partially elastic tensile member attachable at ends at least indirectly to the user's feet, the second elongate and at least partially elastic tensile member slidably traversing the elongate lower channel,
said shoulder straps or loops overlapping and in contact with one another at a crossing, said shoulder straps or loops being continuous with a strap segment that overlaps and engages said shoulder straps or loops at said crossing, said strap segment being freely movable relative to said shoulder straps or loops at said crossing.

16. The wearable device defined in claim 15, wherein said shoulder straps or loops are fixed to one another at said crossing said crossing being spaced from said belt.

17. The wearable device defined in claim 15 wherein said shoulder straps or loops are end portions of a single continuous strap or band, said strap segment being a middle segment of said single continuous strap or band that is continuous on opposite ends with said end portions, said elongate strip attached to and extending along and in contact with said middle segment.

18. The wearable device defined in claim 17, wherein said single continuous strap or band, including said end portions and said middle segment, and said back portion of said belt are devoid of rigid elements.

* * * * *